United States Patent
Viavattine et al.

(10) Patent No.: US 12,034,171 B2
(45) Date of Patent: Jul. 9, 2024

(54) ENERGY STORAGE DEVICE ASSEMBLIES

(71) Applicant: Medtronic, Inc., Minneapolis, MN (US)

(72) Inventors: Joseph J. Viavattine, Vadnais Heights, MN (US); Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 819 days.

(21) Appl. No.: 17/093,361

(22) Filed: Nov. 9, 2020

(65) Prior Publication Data

US 2022/0149339 A1   May 12, 2022

(51) Int. Cl.
| | |
|---|---|
| *H01M 50/183* | (2021.01) |
| *A61N 1/362* | (2006.01) |
| *H01M 10/42* | (2006.01) |
| *H01M 50/116* | (2021.01) |
| *H01M 50/557* | (2021.01) |
| *H01M 50/60* | (2021.01) |

(52) U.S. Cl.
CPC ........ *H01M 50/183* (2021.01); *A61N 1/3625* (2013.01); *H01M 50/116* (2021.01); *H01M 50/557* (2021.01); *H01M 50/60* (2021.01); *H01M 10/4228* (2013.01)

(58) Field of Classification Search
CPC .. H01M 50/183; H01M 50/60; H01M 50/116; H01M 50/557; H01M 10/42; H01M 10/4228; A61N 1/3625
See application file for complete search history.

(56) References Cited

U.S. PATENT DOCUMENTS

| | | | |
|---|---|---|---|
| 5,173,375 A * | 12/1992 | Cretzmeyer | ........ H01M 50/147 |
| | | | 429/185 |
| 6,048,638 A | 4/2000 | Pendalwar | |
| 7,150,936 B2 | 12/2006 | Tukawaki et al. | |
| 7,579,106 B2 | 8/2009 | Haas et al. | |
| 9,214,696 B2 * | 12/2015 | Min | ...................... H01M 10/52 |
| 10,036,385 B2 | 7/2018 | Triebe | |
| 2002/0106555 A1 | 8/2002 | Langan | |
| 2015/0207182 A1 | 7/2015 | Tsukui | |
| 2018/0166747 A1 | 6/2018 | Mouchawar et al. | |

FOREIGN PATENT DOCUMENTS

| | | |
|---|---|---|
| CN | 1731598 A | 2/2006 |
| CN | 107631844 A | 1/2018 |
| CN | 108039423 A | 5/2018 |

(Continued)

OTHER PUBLICATIONS

International Search Report and Written Opinion of International Application No. PCT/US2021/050200, dated Jan. 5, 2022, 10 pp.

*Primary Examiner* — Karie O'Neill Apicella
(74) *Attorney, Agent, or Firm* — Shumaker & Sieffert, P.A.

(57) ABSTRACT

In some examples, a method for forming an energy storage device assembly, e.g., for an implantable medical device, may comprise partially enclosing electrodes of an energy storage device within a foil pack, wherein the foil pack includes an unsealed portion and a sealed portion when partially enclosing the electrodes of the energy storage device. The method may further comprise forming a first heat seal at the unsealed portion of the foil pack, and subsequently forming a second heat seal that is redundant with the first heat seal of the foil pack.

20 Claims, 9 Drawing Sheets

(56) References Cited

FOREIGN PATENT DOCUMENTS

| | | |
|---|---|---|
| CN | 208873781 U | 5/2019 |
| CN | 110190207 A | 8/2019 |
| CN | 209447850 U | 9/2019 |
| CN | 209455293 U | 10/2019 |
| CN | 108692888 B | 11/2019 |
| EP | 1772914 A2 | 4/2007 |
| EP | 2648259 A2 | 10/2013 |

* cited by examiner

ENERGY STORAGE DEVICE ASSEMBLIES

TECHNICAL FIELD

This disclosure is related to energy storage device assemblies for use, e.g., in medical devices.

BACKGROUND

Energy storage devices such as batteries and capacitors may be employed in medical devices to provide operational power. In the examples, the energy storage devices may include electrochemical cells that function to provide and/or store energy. In some examples the energy storage devices may be enclosed by foil packs that are configured to isolate or otherwise separate components of the electrochemical cell from an environment surrounding an exterior of the foil pack. A heat-sealing process may be employed to seal portions of the foil pack once the energy storage device has been located within the foil pack.

SUMMARY

In one example, the disclosure related to a method comprising partially enclosing electrodes of an energy storage device within a foil pack, wherein the foil pack includes an unsealed portion and a sealed portion when partially enclosing the electrodes of the energy storage device; forming a first heat seal at the unsealed portion of the foil pack; and subsequently forming a second heat seal that is redundant with the first heat seal of the foil pack.

In another example, the disclosure relates to an energy storage device assembly comprising electrodes; an electrolyte; and a foil pack having an enclosure that encloses the electrolyte and at least a portion of the electrodes, wherein the enclosure of the foil pack includes a first heat sealed portion and a second heat sealed portion that is redundant with the first heat seal portion.

The details of one or more examples are set forth in the accompanying drawings and the description below. Other features, objects, and advantages will be apparent from the description and drawings, and from the claims.

DETAILED DESCRIPTION

In some examples, the disclosure describes example assemblies including a foil pack and an energy storage device enclosed by the foil pack, and techniques for making such assemblies.

A variety of medical devices may utilize one or more energy storage devices as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to energy storage device assemblies including batteries that are employed in IMDs that provide cardiac rhythm management therapy. However, as will be apparent from the description herein, examples of the disclosure are not limited to IMDs that provide such therapy. For example, in some instances, one or more of the example energy storage assemblies described herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example energy storage assemblies of this disclosure may be employed in medical devices configured to monitor one or more patient physiological parameters, e.g., by monitoring electrical signals of the patient, alone or in conjunction with the delivery of therapy to the patient. Furthermore, example energy storage assemblies of the disclosure are not limited to medical devices and may be employed in any device in which such an energy storage assembly may be used to supply operational power to the device from a sealed foil pack enclosure.

A foil pack enclosing the components the energy storage device (e.g., electrodes and electrolyte) may be employed to fluidly isolate the energy storage device from an environment surrounding an exterior of the foil pack. For example, the energy storage device may be configured for placement within the housing of a larger device such as an implantable medical device or other device, with the foil pack substantially isolating the energy storage device from other components within the housing of the larger device. The foil pack may provide a hermetic and/or liquid tight boundary depending on the device requirements and design.

In some examples, the components of an energy storage device, e.g., the electrodes, may be partially enclosed by a foil pack with a sealed portion and another portion of the foil pack being unsealed. For example, a heat seal process may be used to seal two opposing laminate foil substrates to each other to form a foil pack containing the energy storage device with one or more unsealed areas between the foil substrates. Using the unsealed portion, a leak test may be carried out through a test port to evaluate the integrity of a sealed portion of the foil pack. For example, a helium gas may be filled in the pack and leaks in the sealed portion may be detected by detecting helium leaking from the foil pack in the area of the sealed portion down to levels below $10^{-8}$ mbar l/sec (helium equivalent rate) to ensure long term reliability in the device. Following the leak test, the foil pack may be filled with a liquid electrolyte (e.g., via the test port) around the electrodes and the unsealed portion of the foil pack may be sealed, e.g., using a heat seal process, and any excess portion of the foil pack may be removed.

However, such a process may not allow for this final seal of the foil pack to be easily tested for leaks in such a manner. For example, verifying that the foil pack containing the energy storage device components (e.g., that form the electrochemical cell) is sufficiently hermetic and/or liquid tight may be challenging after the foil pack is filled with electrolyte and then sealed. Additionally, forms of leak check that attempt to observe the leak of battery electrolyte materials directly may be limited to ranges of $10^{-6}$ mbar l/sec (helium equivalent rate) which, is some example, are not desirable to demonstrate hermetic needs of devices with, e.g., 10 plus year longevities. A check of the pre-filled hermeticity and/or liquid tightness is less challenging (e.g., using the process described above) but creating the final seal may be challenging, e.g., considering that the presence of the electrolyte in or near the final seal my interfere/interact with the final sealing process.

In accordance with examples of the present disclosure, energy storage device assemblies according to the disclosure may include foil packs having one or more redundant seals formed around all or a portion of the energy storage device. For example, in the case of a foil pack having an unsealed portion defining a port used for a leak testing and/or filling an electrolyte as described above, a heat seal process may be used to form a first seal of the test port of the foil pack. A second heat seal may then be formed that is redundant with the first heal seal to improve the integrity of the combined seal of the fill/test port. The redundancy may increase the likelihood of a satisfactory overall final sealing of the foil pack. For example, assuming that each heat seal already has a relatively high likelihood of satisfactory seal individually, by using a redundant heat seal configuration the overall probability of at least one of the original first seal and redundant second seal being satisfactory may increase the likelihood of a satisfactory seal to a point where a leak test is no longer needed or desirable. For example, with two heat seals that are each individually 99% effective, the combination of the two redundant seals would be 99.99% effective. In some examples, a third heat seal that is redundant with the first two heat seals may be employed or even more than three total seals may be employed (e.g., a total of four heat seals).

In some examples, to evaluate the integrity of the final sealing process, a helium source (e.g., helium bombed glass spheres) may be positioned between the first seal and the second seal, e.g., after the first seal has been formed but prior to formation of the second seal. After forming the second seal of the foil pack, the integrity of the second seal may be checked by monitoring for helium escaping the second seal.

Figure 1:
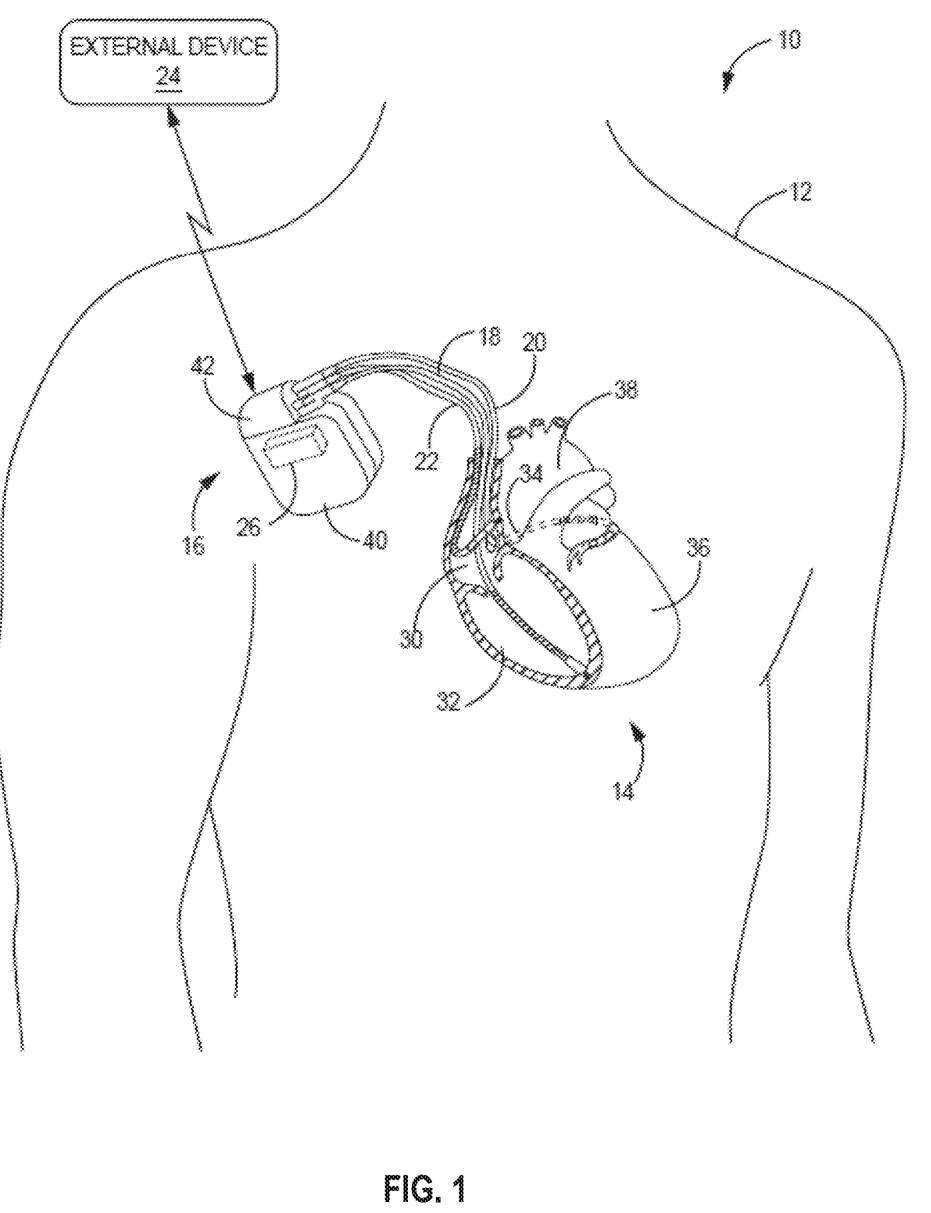
FIG. 1 is a conceptual diagram that illustrates an example medical device system that may be used to deliver therapy to a patient.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has energy storage device assembly 26 positioned within an outer housing 40 of the IMD 16. Energy storage device assembly 26 may function as a battery (e.g., primary or secondary) or capacitor assembly including one or more electrochemical cells that supply operational power for IMD 16. As described further below, energy storage device assembly 26 includes foil pack 50 that encloses components of an electrochemical cell such as electrodes (anode and cathode) and an electrolyte.

While the examples in the disclosure are primarily described with regard to energy storage device assembly 26 positioned within housing 40 of IMD 16 for delivery of electrical therapy to heart of patient 12, in other examples, energy storage device assembly 26 may be utilized with other implantable medical devices. For example, energy storage device assembly 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), or the like.

Moreover, while examples of the disclosure are primarily described with regard to implantable medical devices, examples are not limited as such. Rather, some examples of the energy storage device assemblies described herein may be employed in any medical device including non-implantable medical devices. For example, an example energy storage device assembly may be employed to supply power to a medical device configured delivery therapy to a patient externally or via a transcutaneously implanted lead or drug delivery catheter the requires a high reliability power source.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition(s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMB 16 in order to monitor electrical activity of heart 14. In one example, the sensing circuitry may include switching circuitry to select which of the available electrodes on leads 18, 20, and 22 of IMB 16 are used to sense the heart activity. Additionally, the sensing circuitry of IMB 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as energy storage device assembly 26, which may include a lithium primary battery. Energy storage device assembly 26 may be capable of holding a charge for several years. In general, energy storage device assembly 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, or delivery of a therapeutic drug fluid. Energy storage device assembly 26 may include foil pack 50 that encloses one or more lithium-containing anodes and cathodes including an active material that electrochemically reacts with the lithium within an electrolyte to generate power.

Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels) until a fibrillation of heart 14 is stopped. IMD 16 may detect fibrillation by employing one or more fibrillation detection techniques known in the art. For example, IMD 16 may identify cardiac parameters of the cardiac signal (e.g., R-waves), and detect fibrillation based on the identified cardiac parameters.

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 42. For example, leads 18, 20, and 22 are connected to IMD 16 using the lead connector ports in connector block 42. Once connected, leads 18, 20, and 22 are in electrical contact with the internal circuitry of IMD 16. Energy storage device assembly 26 may be positioned within the outer housing 40 of IMD 16. Housing 40 may be hermetically sealed and biologically inert. In some examples, outer housing 40 may be formed from a conductive material. For example, housing 40 may be formed from a material including, but not limited to, titanium, stainless steel, among others.

Figure 2:
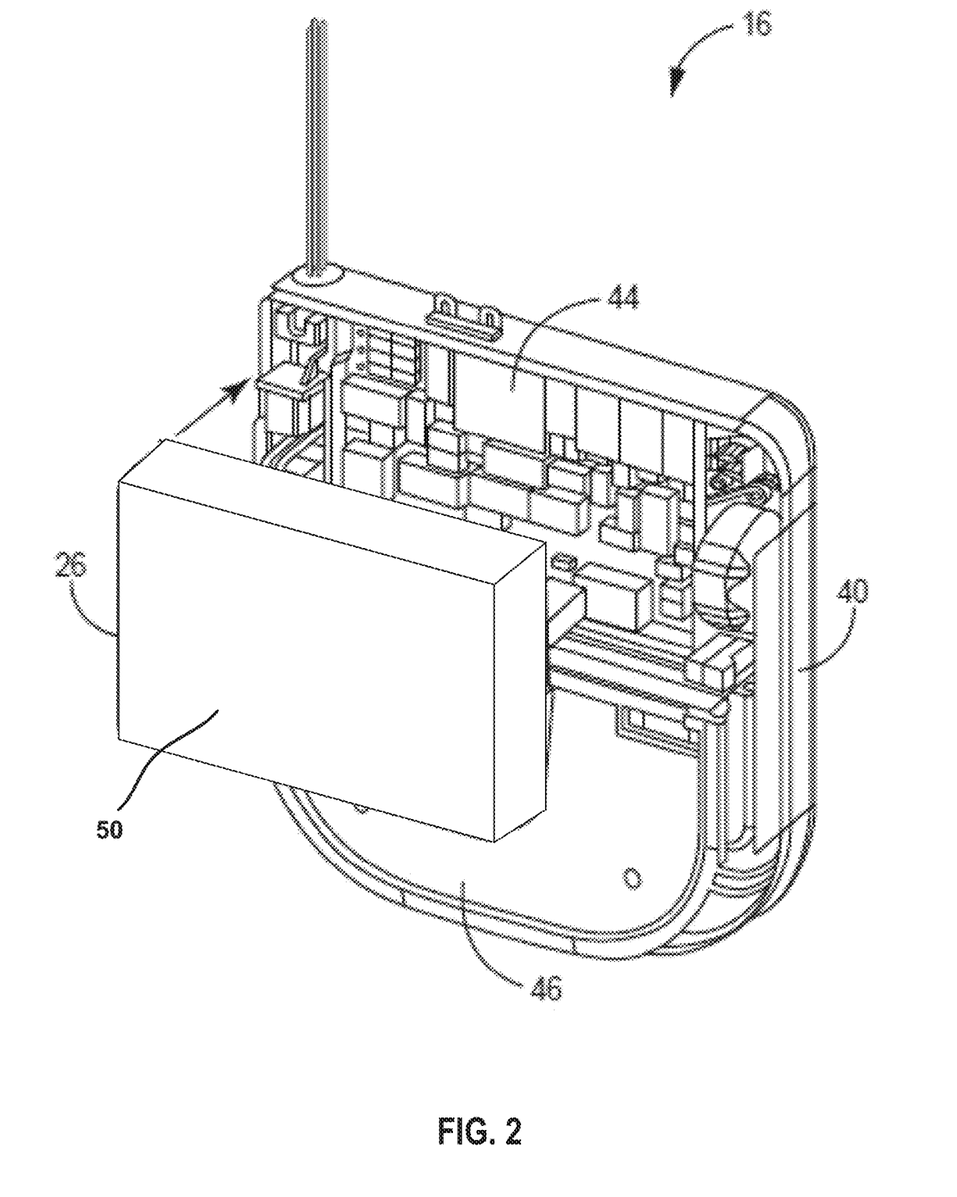
FIG. 2 is a conceptual diagram illustrating a partial exploded view of the IMD of FIG. 1.

FIG. 2 is a conceptual diagram of IMD 16 of FIG. 1 with connector block 42 not shown and a portion of outer housing 40 removed to illustrate some of the internal components within housing 40. IMD 10 includes outer housing 40, a control circuitry 44 (which may include processing circuitry), energy storage device assembly 26 (e.g., including an organic electrolyte battery) and capacitor(s) 46. Control circuitry 44 may be configured to control one or more sensing and/or therapy delivery processes from IMD 16 via leads 18, 20, and 22 (not shown in FIG. 2). Energy storage device assembly 26 includes foil pack 50 disposed around (e.g., forming a liquid and/or hermetic enclosure) one or more electrochemical cells that provide operational power to IMD 16. In the example IMD 16 of FIG. 2, energy storage device 26 charges capacitor(s) 46 and powers control circuitry 44.

During fabrication of energy storage device assembly 26, two laminated foil substrates may be positioned with electrodes between them. Multiple heat seals may be used to form foil pack 50 to enclose the electrodes (and electrolyte) within foil pack 50. As described herein, one or more redundant heat seals may be formed during the process around all or a portion of a heat-sealed perimeter of foil pack 50.

Figure 3:
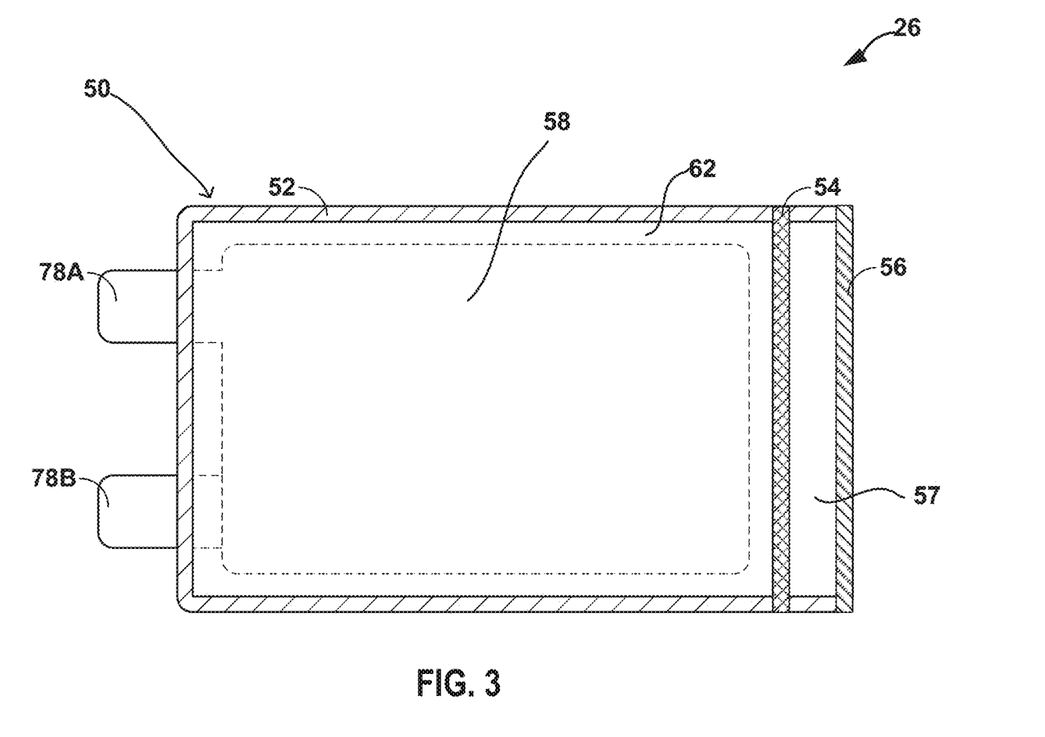
FIG. 3 is a conceptual schematic diagram illustrating an example energy storage device assembly in accordance with an example of the disclosure.
Figure 4:
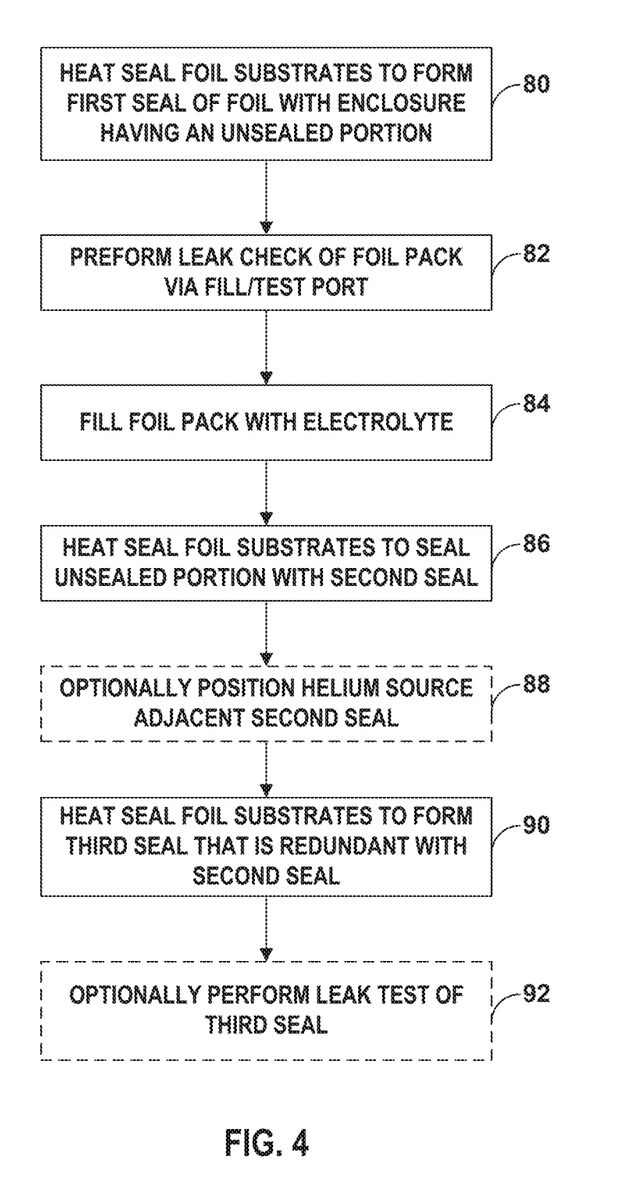
FIG. 4 is a flow diagram illustrating an example technique for forming an energy storage device assembly in accordance with an example of the disclosure.

FIG. 3 is a conceptual schematic diagram illustrating an example energy storage device assembly 26 in accordance with examples of the disclosure. FIG. 4 is a flow diagram illustrating an example technique for assembling energy storage device assembly 26. FIGS. 5A-5D are conceptual schematic diagrams illustrating assembly 26 at various intermediate points during the assembly process, e.g., according to the technique of FIG. 4. FIG. 6 is a conceptual schematic diagram illustrating energy storage device assembly 26 along cross-section A-A indicated in FIG. 5B.

As shown in FIGS. 3 and 6, assembly 26 includes foil pack 50 enclosing first and second electrodes 58A and 58B (collectively "electrodes 58") and separator 60, which is positioned between electrodes 58A and 58B within enclosure 62. Although not shown, an electrolyte such as a liquid electrolyte may be present within enclosure 62 defined by foil pack 50 such that the electrolyte surrounds electrodes 58 and separator 60. Together, the electrolyte and electrodes 58 may form an electrochemical cell that provide operational power to IMD 16. In some examples, the electrochemical cell defined by electrodes 58, separator 60, and the electrolyte in enclosure 62 may be a lithium ion cell.

First electrode 58A may define an anode and include an anode current collector and active anode material (e.g., in the form of a conductive plate coated with an active anode material). Second electrode 58B may define a cathode and include a cathode current collector and active cathode material (e.g., in the form of a conductive plate coated with an active cathode material). Example materials for the current collector portions of electrodes 58 may include copper, aluminum, titanium, nickel and/or the like. Example active materials for an anode may include lithium, graphite, lithium titanate and/or the like. Example active materials for a cathode may include silver vanadium oxide, CFx, MnO2, and mixtures of thereof. Example electrolyte that may be employed in the electrochemical cell may include organic electrolytes containing lithium hexafluoroarsenate salt. Other materials are contemplated.

Although the example of FIGS. 3, 5A-5D, and 6 includes only two plates that form electrodes 58 (one anode plate and one cathode plate, in other examples, electrodes 58 may include multiple anode plates and/or multiple cathode plates, e.g., in a stacked configuration, that are electrically coupled to each other. In some examples, electrodes 58 may have a rolled configuration or other suitable electrode configuration rather than a stacked plate configuration.

First electrode 58A include first tab 78A located outside of enclosure 62 of foil pack 50. First tab 78A is electrically coupled to first electrode 58A, e.g., as an integral portion of a metal substrate that is part of first electrode 58A or a separate conductive portion that has been connected (e.g., welded) to the metal substrate that is part of first electrode 58A in enclosure 62. Similarly, second electrode 58B includes second tab 78B located outside of enclosure 62 of foil pack 50. Second tab 78B is electrically coupled to second electrode 58B, e.g., as an integral portion of a metal substrate that is part of second electrode 58B or a separate conductive portion that has been connected (e.g., welded) to the metal substrate that is part of second electrode 58B in enclosure 62. In this manner, first tab 78A and second tab 78B allow for electrical signals to be conducted from inside of enclosure 62 defined by foil pack 50 to components outside of foil pack 50 (e.g., to provide operational power to electrical circuitry of IMD 16).

Foil pack 50 includes first foil substrate 66A and second foil substrate 66B (on top and bottom, respectively, of electrodes 58 and separator 60 in the orientation shown in FIG. 6) which are heat sealed to each other along first heat seal 52, second heat seal 54, and third heat seal 56. First foil substrate 66A and second foil substrate 66B may each have any suitable thickness such as about 0.003 inches to about 0.008 inches. Other thicknesses are contemplated.

Although not shown, first and second foil substrates 66A, 66B may have a laminate or multi-layer structure that allows for substrates 66A and 66B to be heat sealed to each other. For example, first foil substrate 66A and second foil substrate 66B may each include a metallic layer with a polymer layer on either side of the metallic layer. The metallic layer may be any suitable material such as aluminum or stainless steel, and may function as a barrier layer for foil pack 50. The polymer layer on the side of the metallic layer that bonds to the opposing substrate (the polymer layer that bonds with the opposing substrate) may be a polyolefin such as polyethylene (PE) although other polymer materials are contemplated. The polymer material may be melt-able/ bondable via the application of heat (e.g., at a temperature above the melting point of the polymer) and/or electrically insulating. The polymer layer on the side of the metallic layer opposite the bonding interface may include stronger higher melting material such as a polyester (PET) although other polymer materials are contemplated. The polymer material may add strength to the foil pack 50 and/or may also be electrically insulating. The structure of first foil substrate 66A and second foil substrate 66B may allow for first foil substrate 66A and second foil substrate 66B to be bonded to each other via a heat-sealing process. The description for the metals, thicknesses, and polymer layers are exemplary, and other suitable examples are contemplated. The techniques described herein may apply regardless of the particle foil and lamination type selected.

In the area of first tab 78A, rather than being bonded or otherwise heat sealed to each other directly, first foil substrate 66A may be sealed to an upper surface of first tab 78A and second foil substrate 66B may be sealed to the opposing lower surface of second tab 78A so that first tab 78A is between first foil substrate 66A and second foil substrate 66B for a portion of first heat seal 52. In this manner, first tab 78A may extend out of foil pack 50 for those reasons described above. The same configuration may be used to seal foil pack 50 around second tab 78B with first heat seal 52.

First heat seal 52, second heat seal 54, and third heat seal 56, in combination, may define a substantially hermetic and/or fluid tight seal for enclosure 62, with third heat seal 56 being redundant with second heat seal 54. Third heat seal 56 may be considered redundant with second heat seal 54 in that enclosure 62 may remain substantially hermetic and/or fluid tight even if second heat seal 54 includes one or more portions in which the seal fails (e.g., during the heat seal process and/or during the life of assembly 26) as long as third heat seal 56 provides a substantially hermetic and/or fluid tight seal. Likewise, second heat seal 54 may be considered redundant with third heat seal 56 in that enclosure 62 may remain substantially hermetic and/or fluid tight even if third heat seal 56 includes one or more portions in which the seal fails (e.g., during the heat seal process and/or during the life of assembly 26) as long as second heat seal 54 provides a substantially hermetic and/or fluid tight seal. By providing one or more redundant heat seals along all or a portion of entire perimeter of enclosure 26 defined by foil pack 50, the likelihood of enclosure 26 being or becoming non-hermetic and/or non-fluid tight may be decreased. Such a property may be beneficial since, unlike first heat seal 52, it may be difficult to test the integrity of second heat seal 54 after the heat-sealing process, as explained below. Thus, as an alternative, one or more redundant heat seals such as third heat seal 56 may be formed to increase the likelihood of achieving an adequate seal for enclosure 62 of foil pack 50 even without the ability to check the integrity of second heat seal 54.

As noted above, FIG. 4 is a flow diagram illustrating an example technique for forming an example energy storage device assembly such at assembly 26 of FIG. 3. FIGS. 5A-5D are conceptual schematic diagrams illustrating the formation of such an assembly at various intermediate stages of the illustrated technique. For ease of description, the technique of FIG. 4 is described with regard to assembly 26 of FIG. 3. However, such an example may be used to form any suitable energy storage device assembly including a foil pack with at least one redundant seal.

In accordance with some examples of this disclosure, electrodes 58 may be partially enclosed within foil pack 50 with the foil pack including an unsealed portion and a sealed portion. For example, to partially enclose electrodes 58 within foil pack 50 in a such a manner, electrodes 58, with separator 60 between the respective electrodes 58A and 58B, may be placed between first foil substrate 66A and second foil substrate 66B, e.g., in the configuration shown in FIG. 5A. First foil substrate 66A and second foil substrate 66B may then be heat sealed to each other to form first heat seal 52 around at least a portion of electrodes 58 and separator 60, e.g., to partially enclose electrodes 58 and separator 60 withing enclosure 62 in the configuration shown in FIG. 5B (80). Any suitable heat-sealing process may be used to form first heat seal 52. For example, first foil substrate 66A and second foil substrate 66B may be sealed by either a single sided heat source on one side of the seal or an opposed heat source on both sides of the seal. IN the case of substrates having the example multi-layer structure described above, heat conducts through the PET and Al layers to reach the PE layer. The opposing PE layers melt together. Sealing around tabs 78A and 78B more likely warrants opposed heating. Opposed heating can reduce cycle time of the sealing process. As will be described below, after first heat seal 52 is formed, a portion of foil pack 50 remains unsealed to allow for access to enclosure 62 (e.g., with port 64 in first foil substrate 66A allowing for access to enclosure 62 after first seal 52 is formed).

As shown in FIG. 6, a surface of foil substrate 66A may be bonded directly to an opposing surface of second foil substrate 66B in the area of first heat seal 52. In the portion of first heat seal 52 from which first and second tabs 78A and 78B extend out of enclosure 62 of foil pack 50, first foil substrate 66A may be bonded to a surface of first and second tabs 78A and 78B and second foil substrate 66B may be bonded to the opposing surface of first and second tabs 78A and 78B to form a seal.

In some examples, a partial heat seal between first foil substrate 66A and second foil substrate 66B may be formed, e.g., to form an open pouch, prior to positioning electrodes 58 and/or separator 60 in the foil pouch. In such an example, electrodes 58A and 58B may be positioned within the foil pouch with first and second tabs 78A and 78B extending out of the foil pouch and then a seal, e.g., a heat seal, may be formed between first foil substrate 66A and tabs 78A and 78B, as well as between second foil substrate 66B and tabs 78A and 78B.

Figure 5A:
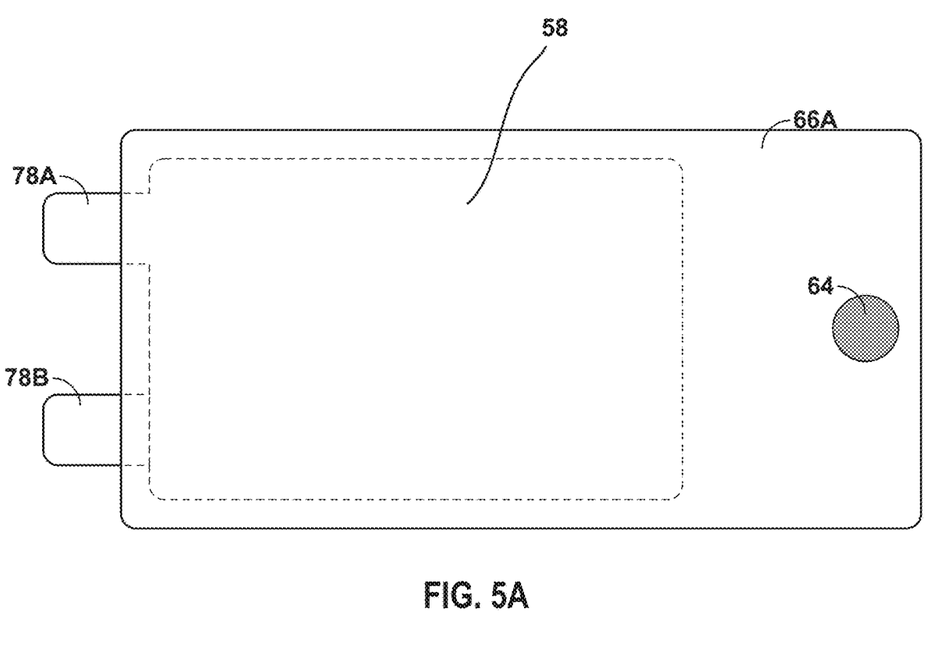
FIGS. 5A-5D are conceptual schematic diagrams illustrating an example article during at various points during a process to assemble the example energy storage device of FIG. 3.
Figure 5B:
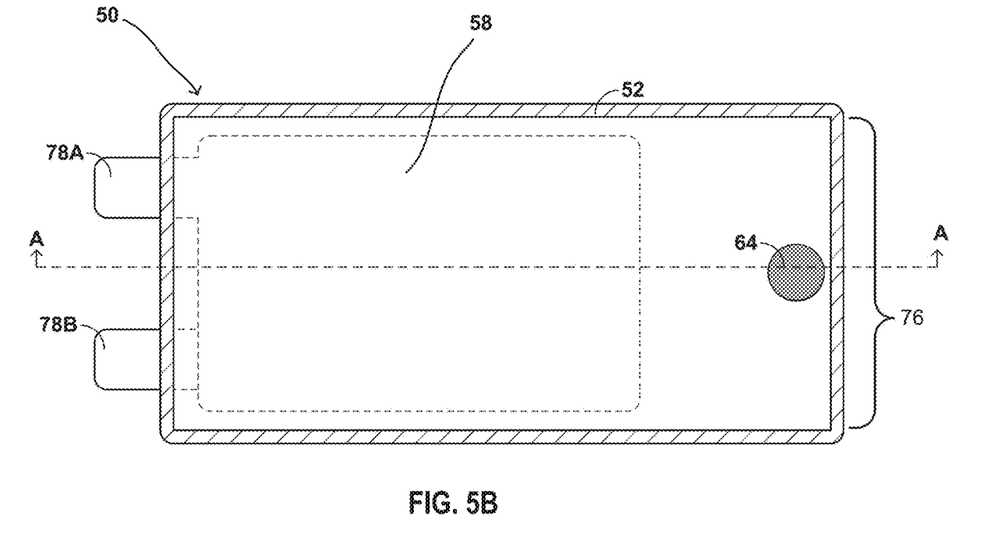
Figure 6:
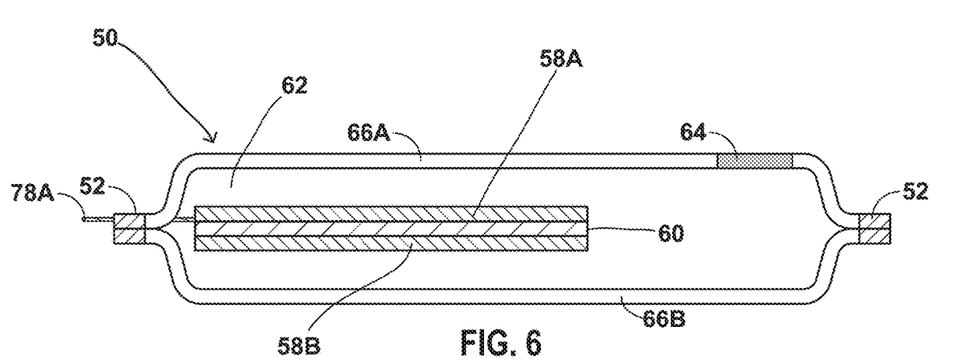
FIG. 6 is a conceptual schematic diagram illustrating a cross-sectional view of the example article shown in FIG. 5B.

As shown in FIG. 5B, first foil substrate 66A includes port 64 which defines an unsealed portion of foil pack 50 allowing for fluid communication between outside enclosure 62 and inside enclosure 62. As described below, port 64 may be used to perform a leak test of first seal 52 and as a fill port to fill enclosure 62 with an electrolyte, such as, a liquid electrolyte. In other examples, portion 76 shown in FIG. 5B of perimeter of foil pack 50 between first foil substrate 66A and second foil substrate 66B may be left unsealed shown. For example, rather than including port 64 in one of first and second foil substrates 58A and 58B, portion 76 of first seal 52 may be left unsealed, e.g., to use for leak testing and/or filling of electrolyte.

As shown in FIG. 4, once first seal 52 has been formed to partially enclose electrodes 58 within foil pack 50, a leak test may be performed to test the integrity of first seal 52, e.g., to determine if first seal 52 has formed a substantially hermetic and/or fluid tight seal (82). Any suitable leak test technique may be employed. In some examples, hollow glass spheres may be prepared with helium (He) through a high pressure "bombing" process. The He-impregnated spheres will start to lose helium when brought to atmospheric pressure. These spheres may be placed in a formed pocked and sealed into the cell a described. Helium will escape and fill the pocket. If there is a leak in the seal, the He will be detectable by a helium leak check machine, e.g., a mass spectrometer.

If it is determined that first heat seal 52 is substantially hermetic and/or fluid tight via the leak test (82), the electrolyte for the energy storage device assembly 26 may be filled in enclosure 62 via port 64 (or other unsealed portion of foil pack 50) (84). Conversely, if it is determined that first heat seal 52 is not substantially hermetic and/or fluid tight, the assembly may be discarded. Alternatively, additional heat seals may be added to replace first heal seal 52. When filled in enclosure 62, the electrolyte may surround electrodes 58 so that the electrolyte and electrodes 58 may function as an electrochemical cell. Suitable electrolytes include those described above. In some examples, to fill enclosure 62 with the electrolyte, a vacuum may be pulled on the empty enclosure and electrolyte may be allowed to flow into the enclosure as the enclosure is brought back to atmospheric pressure. Another option is to use a pressure fill (e.g., after the cell is pulled down to some vacuum level).

Figure 5C:
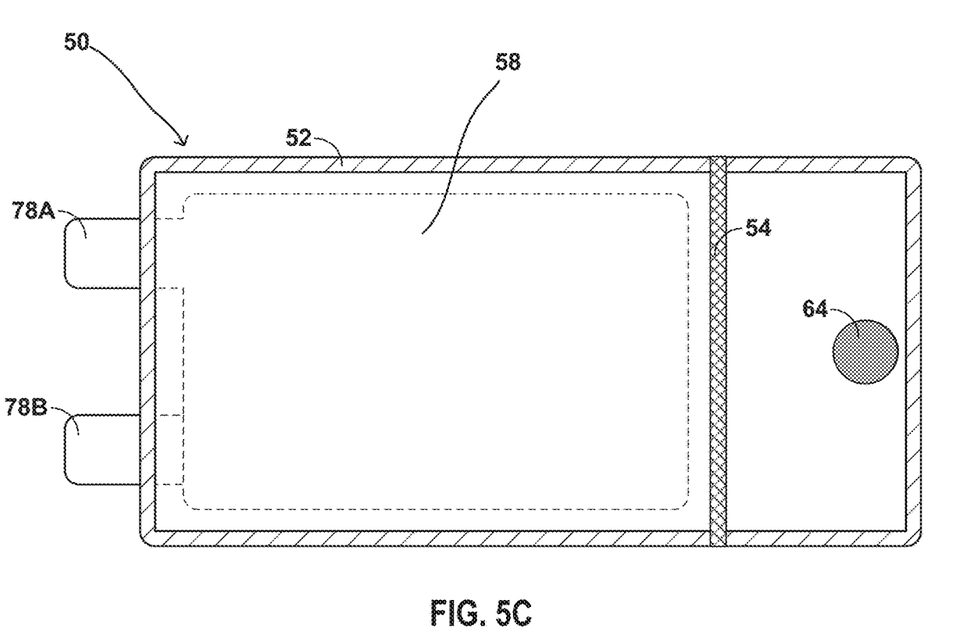

After filling enclosure 62 will a desired amount of electrolyte (as well as optionally wiping or otherwise removing excess electrolyte from foil pack 50 around port 64), another heat-sealing process may be used to form second seal 54 to seal the unsealed portion of foil pack 50 (84). For example, as shown in FIG. 5C, second heat seal 54 may be formed by heat sealing first foil substrate 66A and second foil substrate 66B to each other such that enclosure 62 is substantially hermetically and/or fluidically isolated from port 64. In such a configuration, electrodes 58, separator 62 and electrolyte may be fully sealed within enclosure 62. First seal 52 and second seal 54 combine to form a seal that encloses electrodes 58 (except for tabs 78A and 78B), separator 60 and the electrolyte.

As described above, performing a leak test on second heat seal 54 in the manner described above for first seal 52 may not be possible or practical, e.g., since there is not an unsealed portion. Thus, it may be difficult or not practical to test the integrity of second heat seal 54. Accordingly, as indicated by FIG. 4, another heat-sealing process may be used to form third heat seal 56, which is redundant with second heat seal 56 (90). For example, in the configuration shown in FIG. 5D, third seal 56 may function to seal enclosure 62 from the external environment if second seal 54 does not properly form during the heat sealing process (84) and/or if second seal 54 is broken for some reasons after the heat sealing process.

Using a redundant seal configuration such as that described may help account for the lack of ability to directly test second seal 54 using a leak test such as that described above. For example, if there is a 99.9% chance that second seal 54 is formed as desired (e.g., to be substantially hermetic and/or fluid tight) and, likewise, there is also a 99.9% chance that third seal 56 is formed as desired (e.g., to be substantially hermetic and/or fluid tight), then the likelihood of second and third seals 54 and 56 in combination providing the desired seal may be about 99.9999% (about one in a million).

As show in FIG. 4, in some examples, an optional seal test may be performed on the third seal 56 (92). For example, a helium source (or other detectable gas source) may be located adjacent to second seal 54 outside of enclosure 62 prior to formation of third heat seal 56 (88). The subsequent formation of third heat seal 56 may enclose the helium source within another enclosure 74. The integrity of third seal 56 may then be evaluated by determining whether or not helium from the helium source within enclosure 74 is detectable outside of enclosure 74. Any suitable process may be used to detect the helium including, e.g., those techniques described above for detecting helium during the leak test of first seal 54.

In one example, the helium source may be helium-bombed glass spheres such as those described above. For example, the helium-bombed spheres may be relatively small spheres of material, where the material is relatively permeable to helium. In this way, the helium is bombed in, is retained, and then released at a rate controlled by the diffusion rate of the helium in the glass composition of choice. In some example, the helium bombed spheres having an average diameter of approximately 0.02 inches to about 0.04 inches although other examples are contemplated.

Figure 5D:
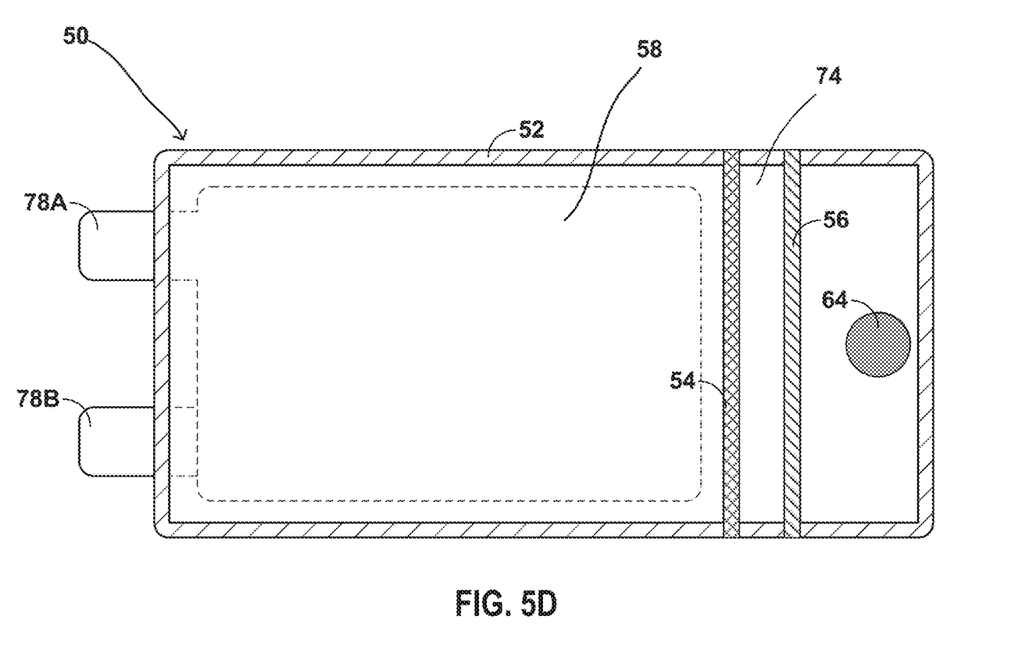

Although not shown in FIG. 4, once the assembly shown in FIG. 5D is formed using the technique of FIG. 4, the excess portion of first foil substrate 66A and second foil substrate 66B not forming enclosure 62 may be trimmed, e.g., by a cutting tool, or otherwise removed. Once removed, energy storage device assembly 26 shown in FIG. 3 may remain.

The configured of energy storage device assembly 26 shown in FIG. 3 in only one example of an assembly including a redundant seal configuration. Although only two seals (second and third heat seals 54 and 56) are used to form redundant sealing of the initially unsealed portion of foil pack 50 in the example of FIG. 3, in some examples, more than two heat seals may be used. For example, in some examples, another heat seal may be formed after the formation of third heat seal 56, where the another heat seal is redundant with second and third heat seals 54 and 56. In this manner, the overall probably of at least one of the heat seals adequately forming a substantially hermetic and/or liquid tight seal may be increased, e.g., as compared to only have second and third seals 54 and 56.

Additionally, in some examples, second heat seal 54 and/or third heat seal 56 may extend across not only the unsealed portion of foil pack 50 to seal the unsealed portion (e.g., port 64). For example, in one example, third heat seal 56 may be formed to completely surround first heat seal 52 and second heat seal 54 so as to function as a redundant seal for both first heat seal 52 and second heat seal 54. In such an example, the leak test described for the example of FIG. 4 may be not be necessary, e.g., based on the presence of one or more heat seals being redundant with first heat seal 52.

Various examples of the disclosure have been described. Any combination of the described systems, operations, or functions is contemplated. These and other examples are within the scope of the following claims.

What is claimed is:

1. A method comprising:
    partially enclosing electrodes of an energy storage device within a foil pack, wherein the foil pack includes an unsealed portion and a first heat seal defining a sealed portion when partially enclosing the electrodes of the energy storage device;
    forming a second heat seal at the unsealed portion of the foil pack; and
    subsequently forming a third heat seal that is redundant with the second heat seal of the foil pack.

2. The method of claim 1, further comprising:
    after forming the second heat seal, adding a helium source to the foil pack adjacent to the second heat seal, wherein forming the third heat seal includes enclosing the helium source between the second heat seal and the third heat seal; and
    determining an integrity of the third heat seal by monitoring for helium from the helium source leaking from the third heat seal.

3. The method of claim 2, wherein the helium source comprises helium bombed glass spheres.

4. The method of claim 1, further comprising, after partially enclosing the energy storage device within the foil pack:
    checking the foil pack via the unsealed portion for a leak in the sealed portion; and
    adding an electrolyte to the foil pack around the electrodes via the unsealed portion prior to forming the second heat seal at the unsealed portion.

5. The method of claim 1, wherein partially enclosing electrodes of an energy storage device within a foil pack comprises heat sealing a first foil substrate to a second foil substrate around at least a portion of an outer perimeter of the electrodes to form the first heat seal that defines the sealed portion.

6. The method of claim 5, wherein the electrodes each include a respective tab portion, and wherein heat sealing the first foil substrate to the second foil substrate around at least the portion of an outer perimeter of the electrodes comprising heat sealing the first foil substrate to the respective tab of each electrode and heating sealing the second foil substrate to the respective tab of each electrode such that the first heat seal is formed over the respective tab portions of the electrodes.

7. The method of claim 5, wherein subsequently forming the third heat seal that is redundant with the second heat seal comprises forming the third heat seal such that the third heat seal is redundant with both the first heat seal and the second heat seal.

8. The method of claim 1, further comprising, after forming the third heat seal, forming a fourth heat seal that is redundant with the second heat seal and the third heat seal.

9. The method of claim 1, wherein the third heat seal surrounds the second heat seal and the sealed portion of the foil pack defined by the first heat seal.

10. The method of claim 1, further comprising trimming an excess portion of the foil pack after forming the third heat seal.

11. An energy storage device assembly comprising:
    electrodes;
    an electrolyte; and
    a foil pack having an enclosure that encloses the electrolyte and at least a portion of the electrodes, wherein the enclosure of the foil pack includes a first heat seal that defines a portion of a perimeter of the enclosure a second heat seal and a third heat seal, wherein the third heat seal is redundant with the second heat seal such that, in case of a failure of the second heat seal, the third heat seal maintains a seal of the enclosure.

12. The assembly of claim 11, further comprising a helium source to the foil pack adjacent to the second heat seal.

13. The assembly of claim 12, wherein the helium source comprises helium bombed glass spheres.

14. The assembly of claim 11, wherein the electrolyte is enclosed in the foil pack by the second heat seal.

15. The assembly of claim 11, wherein the second heat seal is formed before the third heat seal.

16. The assembly of claim 15, wherein the electrodes each include a respective tab portion, and wherein the first heat seal is formed over the respective tab portions of the electrodes.

17. The assembly of claim 16, wherein the third heat seal is redundant with both the first heat seal and the second heat seal.

18. The assembly of claim 11, further comprising a fourth heat seal that is redundant with the second heat seal and the third heat seal.

19. The assembly of claim 11, wherein the third heat seal surrounds the second heat seal and the sealed portion of the foil pack defined by the first heat seal.

20. An implantable medical device including the energy storage device assembly of claim 11.

* * * * *